US012714305B2

(12) United States Patent
Sharifzadeh

(10) Patent No.: US 12,714,305 B2
(45) Date of Patent: Aug. 25, 2026

(54) METHOD FOR ACCURATE MEASUREMENT OF MACULAR PIGMENT OPTICAL DENSITY USING AUTOFLUORESCENCE IMAGING WITH MELANIN CONSIDERATION

(71) Applicant: Mohsen Sharifzadeh, Cottonwood Heights, UT (US)

(72) Inventor: Mohsen Sharifzadeh, Cottonwood Heights, UT (US)

(73) Assignee: LiteAndArt Corp, Cottonwood Heights, UT (US)

(*) Notice: Subject to any disclaimer, the term of this patent is extended or adjusted under 35 U.S.C. 154(b) by 236 days.

(21) Appl. No.: 18/757,450

(22) Filed: Jun. 27, 2024

(65) Prior Publication Data

US 2026/0000292 A1 Jan. 1, 2026

(51) Int. Cl.
*A61B 3/12* (2006.01)
*A61B 5/00* (2006.01)
*G06T 7/00* (2017.01)

(52) U.S. Cl.
CPC .............. *A61B 3/12* (2013.01); *A61B 5/0071* (2013.01); *G06T 7/0012* (2013.01); *A61B 2576/02* (2013.01); *G06T 2207/10064* (2013.01); *G06T 2207/20224* (2013.01); *G06T 2207/30041* (2013.01)

(58) Field of Classification Search
CPC ..... A61B 3/12; A61B 5/0071; A61B 2576/02; G06T 7/0012; G06T 2207/10064; G06T 2207/20224; G06T 2207/30041
See application file for complete search history.

(56) References Cited

U.S. PATENT DOCUMENTS

| | | | |
|---|---|---|---|
| 10,052,019 | B1 | 8/2018 | Jiao et al. |
| 2006/0134004 | A1 | 6/2006 | Gellermann et al. |
| 2006/0244913 | A1 | 11/2006 | Gellermann et al. |
| 2012/0327368 | A1 | 12/2012 | Williams et al. |

(Continued)

OTHER PUBLICATIONS

Beatty, S., et al., "Macular pigment and age related macular degeneration", Brtish Journal of Ophthalmology, 1999; 83, pp. 867-877 (11 pages).

(Continued)

*Primary Examiner* — Stephen R Koziol
*Assistant Examiner* — Michael Kim Maiden
(74) *Attorney, Agent, or Firm* — Michael Pack

(57) ABSTRACT

This invention introduces an improved method for measuring macular pigment optical density (MPOD) using autofluorescence imaging (AFI). Traditional AFI methods often neglect melanin absorption, leading to inaccuracies. The proposed method employs three wavelengths: 488 nm for the main image, 514 nm as a traditional baseline, and 600 nm as an additional baseline to account for melanin absorption. By converting the melanin absorption coefficient from 600 nm to 488 nm and 514 nm, this method ensures precise MPOD measurements. Additionally, a simplified dual-wavelength method is introduced using 488 nm and 600 nm for scenarios requiring less complexity. Both approaches enhance the accuracy of non-invasive retinal imaging by providing a more reliable tool for assessing macular pigment levels and improving our understanding of retinal health.

8 Claims, 9 Drawing Sheets

(56) References Cited

U.S. PATENT DOCUMENTS

| | | | | |
|---|---|---|---|---|
| 2014/0187648 | A1* | 7/2014 | Howard ................ | A61B 5/163 600/300 |
| 2015/0238075 | A1 | 8/2015 | Sharifzadeh et al. | |
| 2022/0351373 | A1 | 11/2022 | Lad et al. | |
| 2025/0185911 | A1 | 6/2025 | Sharifzadeh et al. | |

OTHER PUBLICATIONS

Berendschot, Tos T.J.M. and Dirk van Norren, "Objective determination of the macular pigment optical density using fundus reflectance spectroscopy", Archives of Biochemistry and Biophysics, ScienceDirect, Elsevier, vol. 430, 2004, pp. 149-155 (7 pages).

Bone, Richard A., et al., "Macular pigment, photopigments, and melanin: Distributions in young subjects determined by four-wavelength reflectometry", Vision Research, ScienceDirect, Elsevier, vol. 47, 2007, pp. 3259-3268 (10 pages).

Cideciyan, Artur V., et al., "Autofluorescence Imaging With Near-Infrared Excitation: Normalization by Reflectance to Reduce Signal From Choroidal Fluorophores", Retina, Investigative Ophthalmology Visual Science, vol. 56, 2015, pp. 3393-3406 (14 pages).

Delori, Francois C., "Autofluorescence method to measure macular pigment optical densities fluorometry and autofluorescence imaging", Archives of Biochemistry and Biophysics, ScienceDirect, Elsevier, vol. 430, 2004, pp. 156-162 (7 pages).

Delori, Francois C., "Spectrophotometer for noninvasive measurement of intrinsic fluorescence and reflectance of the ocular fundus", Applied Optics, vol. 33, No. 31, Nov. 1, 1994, pp. 7439-7452 (14 pages).

Delori, Francois C., et al., "Bimodal spatial distribution of macular pigment: evidence of a gender relationship", Journal of the Optical Society of America A, vol. 23, No. 3, Mar. 2006, pp. 521-538 (18 pages).

Delori, Francois C., et al., "Macular pigment density measured by autofluorescence spectrometry: comparison with reflectrometry and heterochromatic flicker photometry", Journal of the Optical Society of America A, vol. 18, No. 6, Jun. 2001, pp. 1212-1230 (19 pages).

Schmitz-Valckenberg, Steffen, et al., "Fundus Autofluorescence and Progression of Age-related Macular Degeneration", Diagnostics and Surgical Techniques, Survey of Ophthalmology, vol. 54, No. 1, Jan.-Feb. 2009, pp. 96-116 (22 pages).

Sharifzadeh, Mohsen, et al. "Nonmydriatic fluorescence-based quantitative imaging of human macular pigment distributions," Journal of the Optical Society of America A, vol. 23, No. 10, Oct. 2006, pp. 2373-2387.

Mainster, Martin A., and Radwan Ajlan, "Clinical Photic Retinopathy: Mechanisms, Manifestations, and Misperceptions", Eds. D.M. Albert et al., Albert and Jakobiec's Principles and Practice of Ophthalmology, Springer Nature Switzerland AG, 2022, DOI https://doi.org/10.1007/978-3-030-42634-7_121, pp. 3777-3806 (30 pages).

Kollias, N "The spectroscopy of human melanin pigmentation," Melanin: Its Role in Human Photoprotection, 1995, Valdenmar Publishing Co. pp. 31-38 (8 pages).

* cited by examiner

METHOD FOR ACCURATE MEASUREMENT OF MACULAR PIGMENT OPTICAL DENSITY USING AUTOFLUORESCENCE IMAGING WITH MELANIN CONSIDERATION

BACKGROUND OF THE INVENTION

The current methods for measuring macular pigment optical density (MPOD) using autofluorescence imaging (AFI) often neglect the impact of melanin in the macula, leading to potential inaccuracies. Traditional AFI methods use two wavelengths, such as 488 nm and 514 nm, where lipofuscin absorbs the excitation light and generates autofluorescence. These methods involve comparing the main image (488 nm) and the baseline image (514 nm) to calculate MPOD by subtracting the baseline from the main image and applying compensation factors based on macular pigment absorption bands. However, these approaches do not account for the absorption by melanin, which can affect the accuracy of MPOD measurements.

Melanin is a significant pigment in the retinal pigment epithelium (RPE) and the macula, especially concentrated in the fovea. Its presence influences optical measurements due to its light absorption properties. Traditional methods fail to isolate the impact of melanin, leading to potential underestimation or overestimation of MPOD.

BRIEF DESCRIPTION OF THE SEVERAL VIEWS OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

The proposed method addresses this limitation by introducing a second wavelength that is absorbed by lipofuscin but not by macular pigment, typically above 550 nm. This wavelength generates lipofuscin autofluorescence and provides a baseline image that includes the influence of melanin. By converting the melanin absorption coefficient from this second wavelength to the 488 nm wavelength, the new method accurately accounts for melanin's impact, ensuring precise MPOD measurements.

This advancement in AFI methodology enhances the accuracy of non-invasive retinal imaging, providing a more reliable tool for assessing macular pigment levels and improving our understanding of retinal health.

Figure 1:
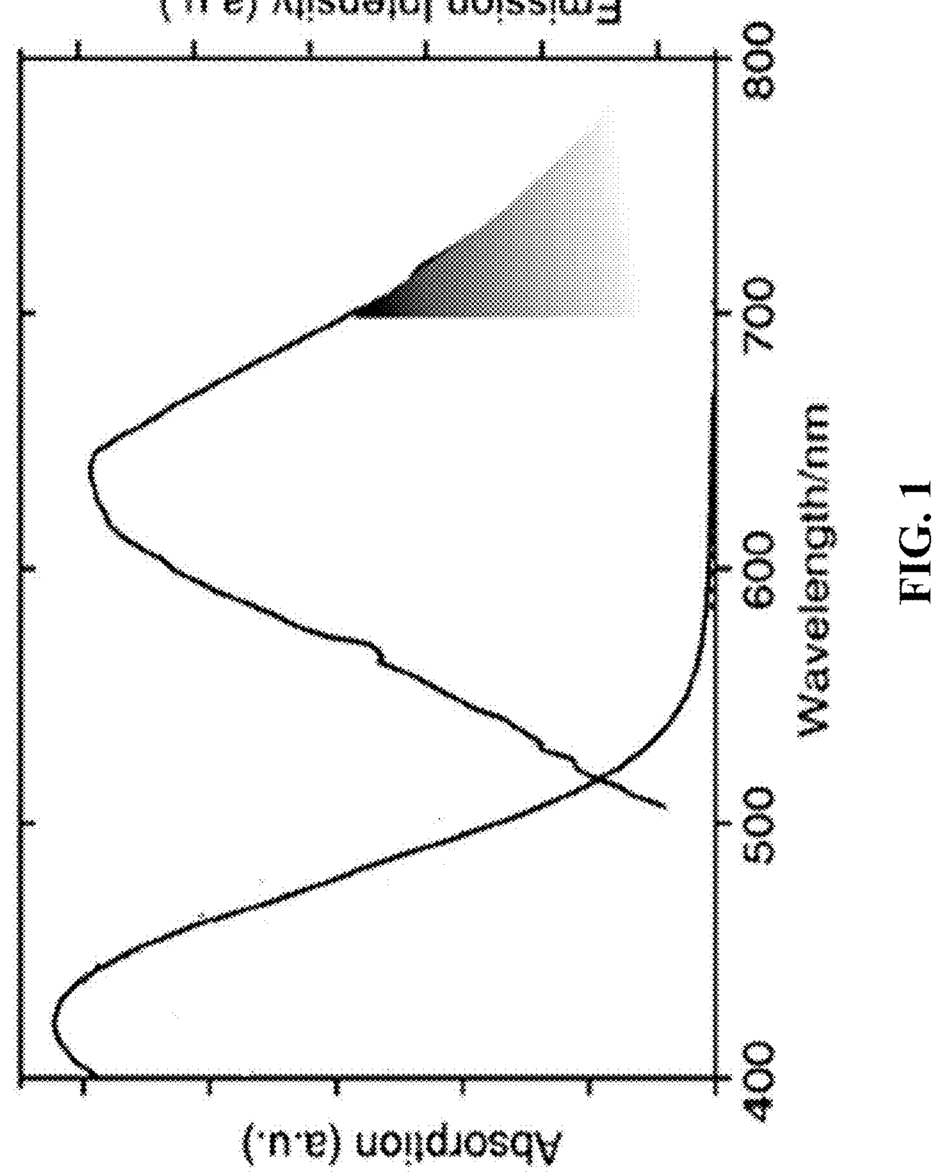
FIG. 1 is a plot of an example of an optical absorption and emission spectra of macular pigment (MP) and lipofuscin.

FIG. 1 illustrates an example of optical absorption spectra of macular pigment (MP) and lipofuscin. The absorption peaks around 488 nm and 532 nm are highlighted, demonstrating the overlap and the need for accurate correction for melanin absorption.

Figure 2:
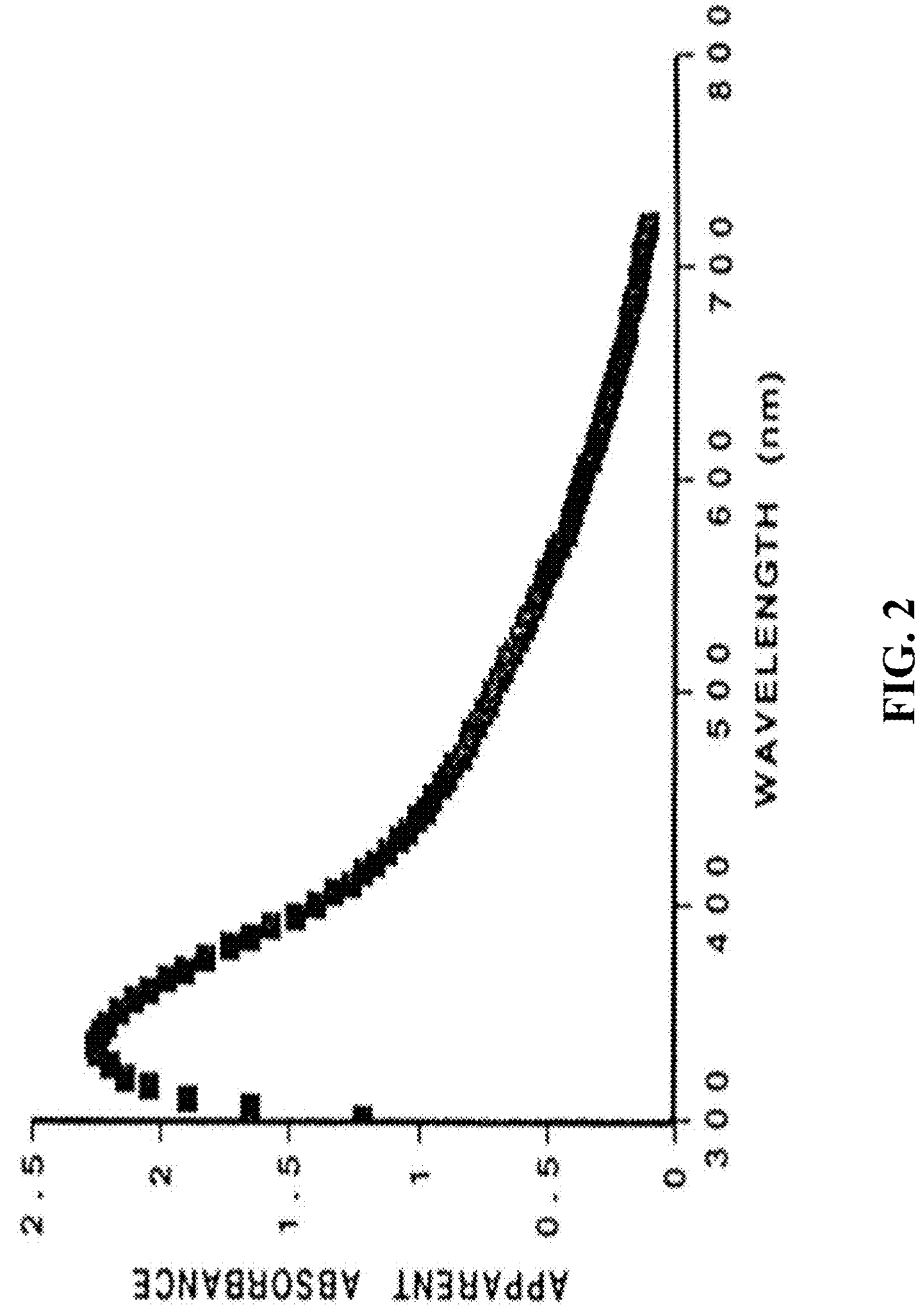
FIG. 2 is a plot of an example of an optical absorption and emission spectra of melanin

FIG. 2 illustrates an example of an optical absorption spectrum of melanin, showing its absorption across a wide range of wavelengths, emphasizing the importance of correcting for melanin absorption in MPOD measurements.

Figure 3:
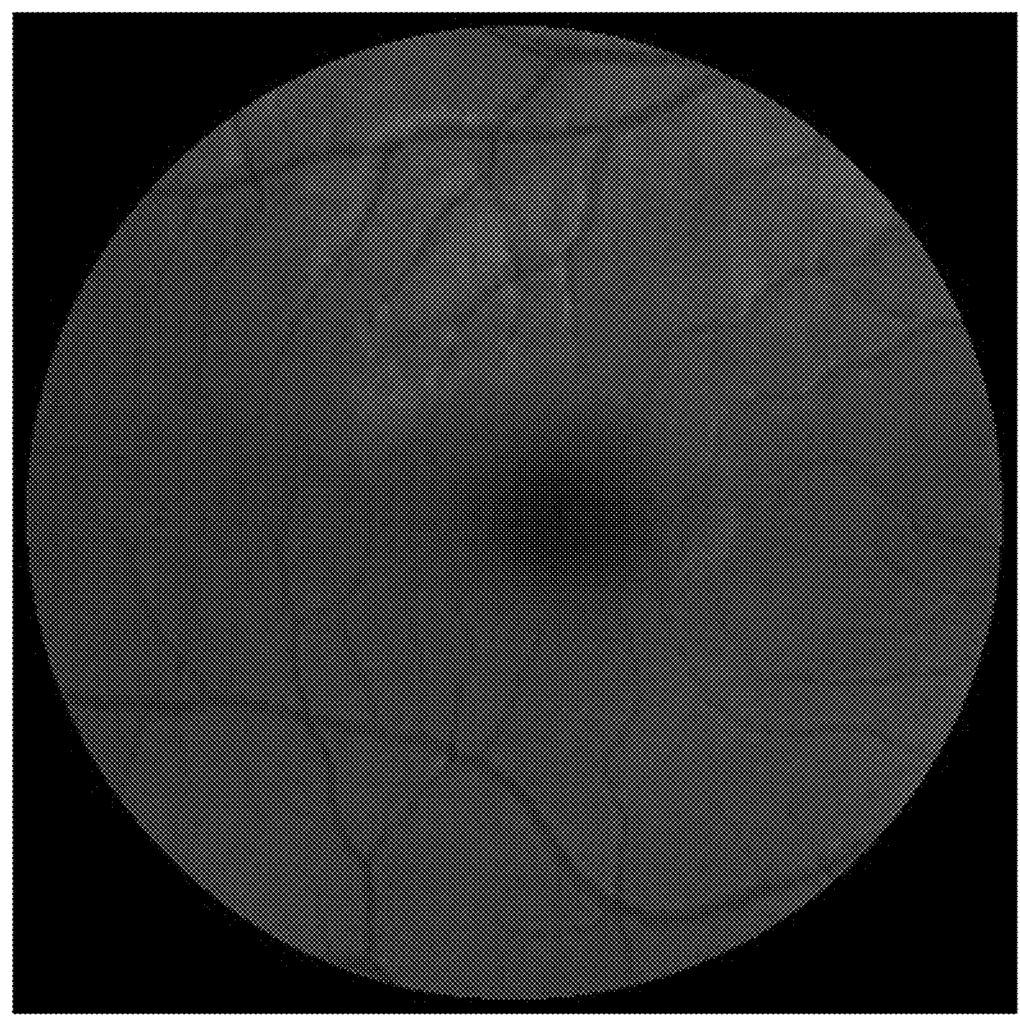
FIG. 3 is an example of an autofluorescence image of the retina obtained with excitation at approximately 488 nm.

FIG. 3 illustrates an example of an autofluorescence image of the macula generated using 488 nm excitation. The light absorbed by macular pigment and lipofuscin generates lipofuscin autofluorescence.

Figure 4:
FIG. 4 is an example of an autofluorescence image of the retina obtained with excitation at approximately 514 nm.

FIG. 4 illustrates an example of an autofluorescence image of the macula generated using 514 nm excitation. This wavelength is also absorbed by macular pigment and lipofuscin, generating lipofuscin autofluorescence.

Figure 5:
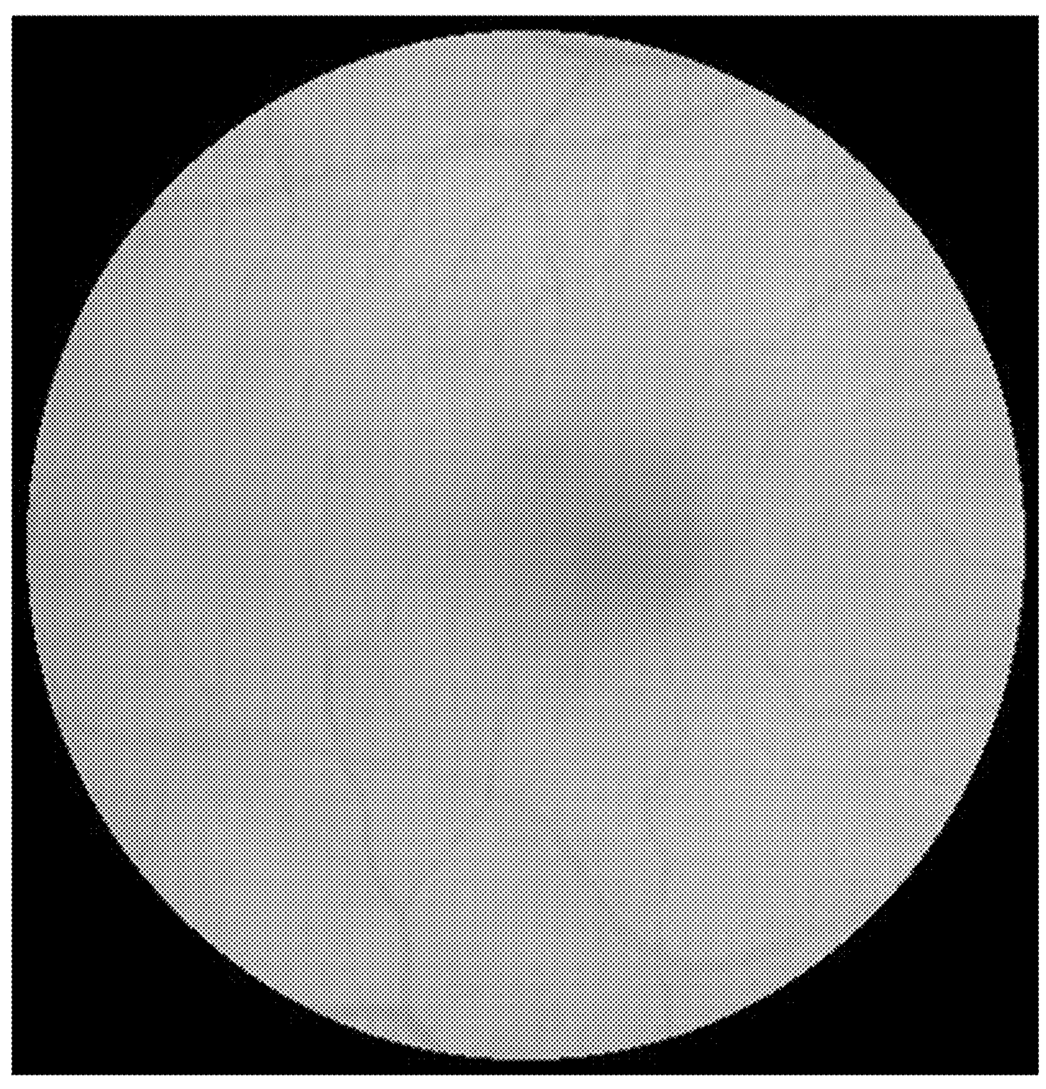
FIG. 5 is an example of an autofluorescence image of the retina obtained with excitation at approximately 600 nm.

FIG. 5 illustrates an example of an autofluorescence image of the macula generated using 600 nm excitation. The light is absorbed by lipofuscin but not by macular pigment, generating lipofuscin autofluorescence and accounting for melanin absorption.

Figure 6:
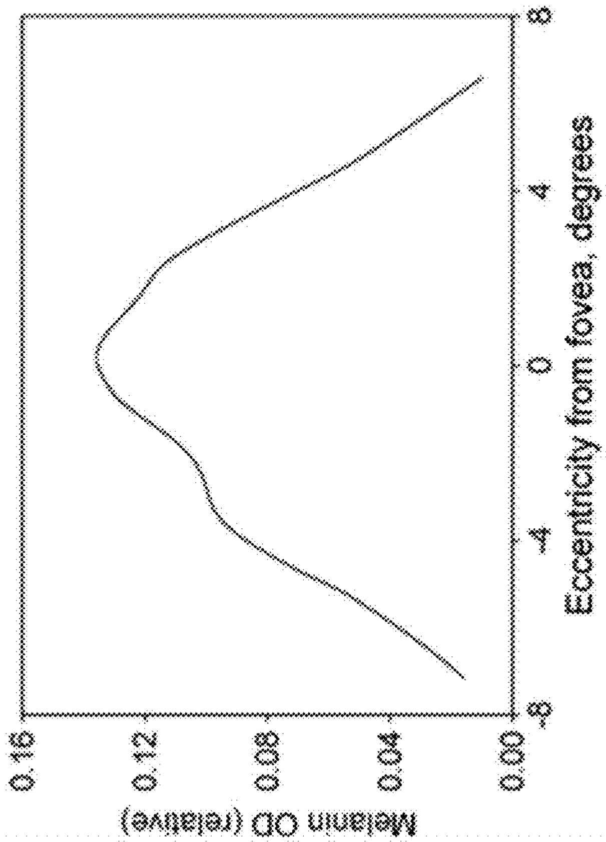
FIG. 6 is a plot of an example lineout of macular pigment optical density and a plot of an example lineout of melanin optical density.
Figure 6:
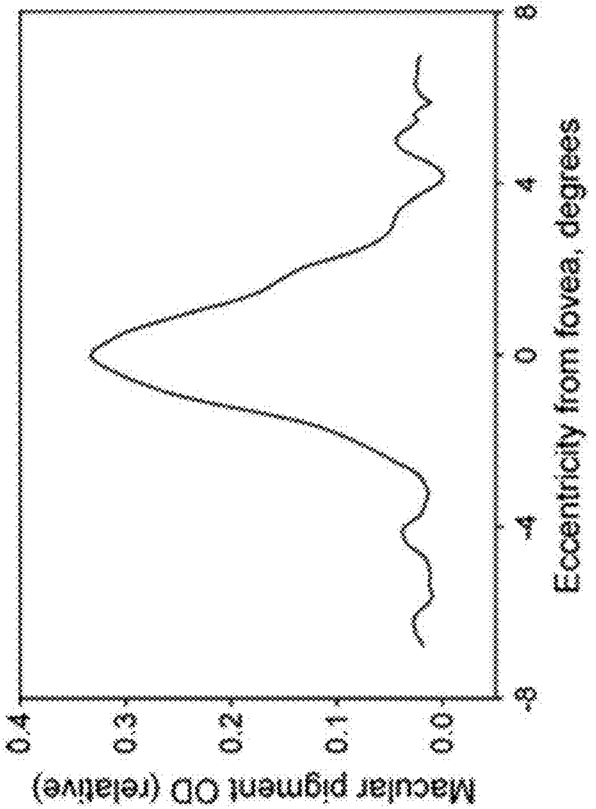

FIG. 6 illustrates an example of a graph showing macular pigment optical density (MPOD) and melanin optical density (OD) in one subject, demonstrating that melanin accounts for approximately 30% of the apparent MPOD. This underscores the importance of correcting for melanin absorption to obtain accurate MPOD measurements.

Figure 7:
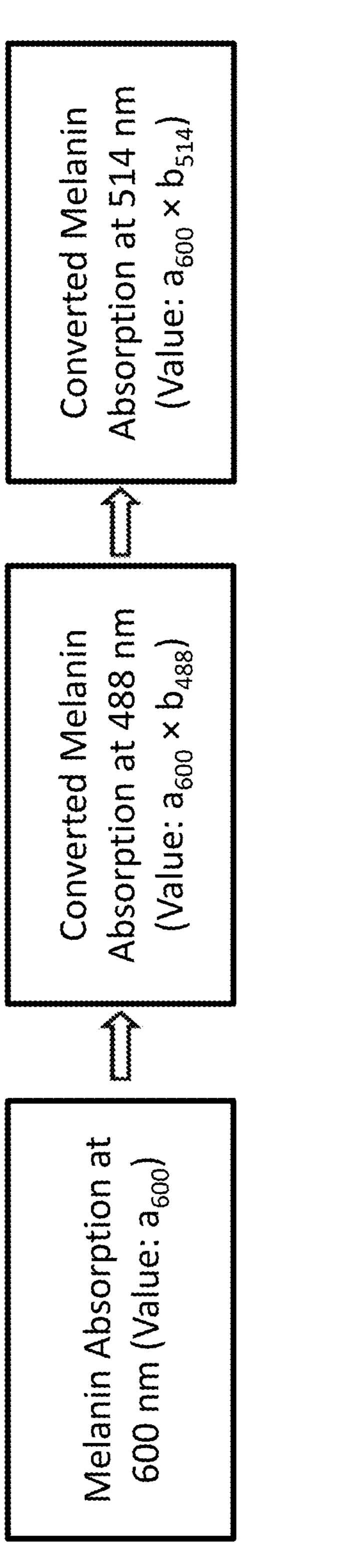
FIG. 7 is a block diagram of an example process for converting melanin absorption measured at one wavelength into equivalent absorption at other wavelengths in accordance with some embodiments of the present technology.

FIG. 7 illustrates an example of a conversion of the melanin absorption coefficient from 600 nm to 488 nm and 514 nm. The absorption at 600 nm is first converted to the equivalent absorption at 488 nm using a compensation factor $b_{488}$, and then converted to the equivalent absorption at 514 nm using a compensation factor $b_{514}$. This process corrects for melanin absorption, ensuring accurate measurement of macular pigment optical density (MPOD).

Figure 8:
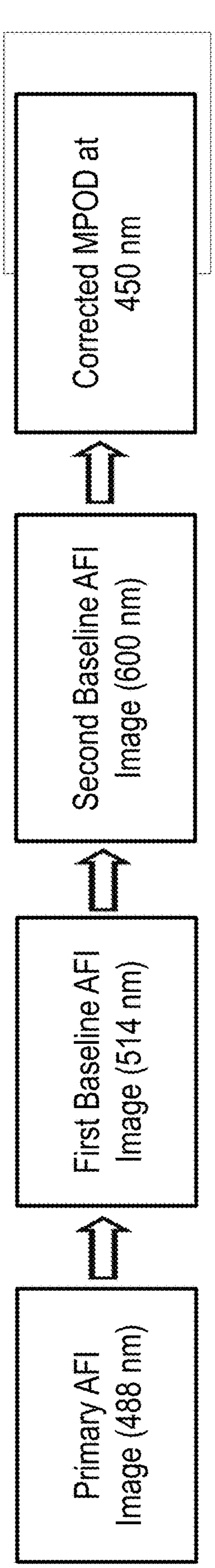
FIG. 8 is a block diagram of an example three-wavelength process for determining macular pigment optical density with melanin compensation in accordance with some embodiments of the present technology.

FIG. 8 illustrates an example of a calculation process for accurate macular pigment optical density (MPOD) measurement using the triple-wavelength approach. The primary AFI image generated at 488 nm is combined with the first baseline AFI image at 514 nm and the second baseline AFI image at 600 nm. The melanin absorption coefficients are converted and subtracted to obtain the corrected MPOD at 450 nm.

Figure 9:
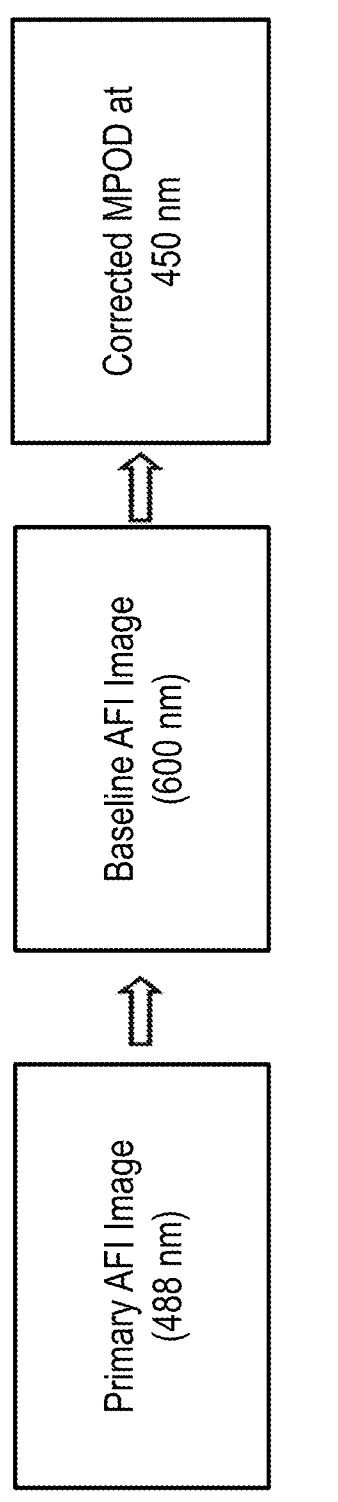
FIG. 9 is a block diagram of an example two-wavelength process for determining macular pigment optical density with melanin compensation in accordance with some embodiments of the present technology.

FIG. 9 illustrates an example of a calculation process for accurate macular pigment optical density (MPOD) measurement using the dual-wavelength approach. The primary AFI image generated at 488 nm is combined with the baseline AFI image at 600 nm. The melanin absorption coefficient is converted and subtracted to obtain the corrected MPOD at 450 nm.

Method 1: Triple-Wavelength Approach

Selection of Wavelengths

Primary Wavelength: 488 nm, absorbed by macular pigment (MP), which includes lutein, zeaxanthin, and meso-zeaxanthin, and lipofuscin, generating lipofuscin autofluorescence.

First Baseline Wavelength: 514 nm, also absorbed by MP and lipofuscin, generating lipofuscin autofluorescence.

Second Baseline Wavelength: 600 nm, absorbed by lipofuscin but not by MP, generating lipofuscin autofluorescence and accounting for melanin absorption.

Generation of Primary and Baseline AFI Images

Barrier Filter: A barrier filter is used to block crystalline lens autofluorescence, ensuring accurate measurement of retinal autofluorescence.

Primary AFI Image: Generated using 488 nm, influenced by both MP and lipofuscin.

First Baseline AFI Image: Generated using 514 nm, influenced by both MP and lipofuscin.

Second Baseline AFI Image: Generated using 600 nm, influenced by melanin and lipofuscin.

Calculation of MPOD Considering Melanin

1. Primary Measurement: Measure MPOD at 488 nm.
2. First Baseline Adjustment: Measure MPOD using 514 nm.
3. Second Baseline Adjustment: Measure melanin absorption using 600 nm.
4. Coefficient Conversion: Convert melanin absorption from 600 nm to 488 nm and 514 nm.
5. Corrected MPOD Calculation: Subtract the converted melanin values from the primary MPOD measurement at 488 nm and 514 nm to find the corrected MPOD at 450 nm.

Mathematical Formulation $$MPOD_{450} = K \cdot \left[ \log\left(\frac{I_{per}}{I_{mac}}\right)_{488} - a \cdot \log\left(\frac{I_{per}}{I_{mac}}\right)_{514} - \left[ b_{488} \cdot \log\left(\frac{I_{per}}{I_{mac}}\right)_{600} + b_{514} \cdot \log\left(\frac{I_{per}}{I_{mac}}\right)_{600} \right] \right],$$

where a is the compensation factor for the absorption coefficient difference between 488 nm and 514 nm, and $b_{488}$ and $b_{514}$ are the compensation factors for converting melanin absorption from 600 nm to 488 nm and 514 nm, respectively.

Method 2: Dual-Wavelength Approach

Selection of Wavelengths

Barrier Filter: A barrier filter is used to block crystalline lens autofluorescence, ensuring accurate measurement of retinal autofluorescence.

Primary Wavelength: 488 nm, absorbed by MP (lutein, zeaxanthin, and meso-zeaxanthin) and lipofuscin, generating lipofuscin autofluorescence.

Baseline Wavelength: 600 nm, absorbed by lipofuscin but not by MP, generating lipofuscin autofluorescence and accounting for melanin absorption.

Generation of Primary and Baseline AFI Images

Primary AFI Image: Generated using 488 nm, influenced by both MP and lipofuscin.

Baseline AFI Image: Generated using 600 nm, influenced by melanin and lipofuscin.

Calculation of MPOD Considering Melanin

1. Primary Measurement: Measure MPOD at 488 nm.
2. Baseline Adjustment: Measure melanin absorption using 600 nm.
3. Coefficient Conversion: Convert melanin absorption from 600 nm to 488 nm.
4. Corrected MPOD Calculation: Subtract the converted melanin value from the primary MPOD measurement at 488 nm to find the corrected MPOD at 450 nm.

Mathematical Formulation $$MPOD_{450} = K \cdot \left[\log\left(\frac{I_{per}}{I_{mac}}\right)_{488}\right] - \left[b_{488} \cdot \log\left(\frac{I_{per}}{I_{mac}}\right)_{600}\right],$$

where K is a constant for the conversion to 450 nm, and $b_{488}$ is the compensation factor for converting melanin absorption from 600 nm to 488 nm.

The invention claimed is:

1. A method for measuring macular pigment optical density (MPOD) using autofluorescence imaging (AFI), comprising:

acquiring a primary AFI image at a first wavelength absorbed by macular pigment and lipofuscin, and determining a primary MPOD measurement based on the primary AFI image;

acquiring a first baseline AFI image at a second wavelength absorbed by macular pigment and lipofuscin, and determining a first baseline MPOD measurement based on the first baseline AFI image:

acquiring a second baseline AFI image at a third wavelength absorbed by lipofuscin but not by macular pigment, and determining a melanin absorption coefficient based on the second baseline AFI image;

converting the melanin absorption coefficient from the third wavelength to the first and second wavelengths to provide converted melanin values; and subtracting the converted melanin values from the primary MPOD measurement and the first baseline MPOD measurement to find a corrected MPOD.

2. The method of claim 1, wherein the first wavelength is 488 nm±5%, the second wavelength is 514 nm±5%, and the third wavelength is 600-nm±5%.

3. The method of claim 1, wherein converting the melanin absorption coefficients includes applying compensation factors for absorption differences between the third wavelength and the first and second wavelengths.

4. A method for measuring macular pigment optical density (MPOD) using autofluorescence imaging (AFI), comprising:

acquiring a primary AFI image at a first wavelength absorbed by macular pigment and lipofuscin, and determining a primary MPOD measurement based on the primary AFI image;

acquiring a baseline AFI image at a second wavelength absorbed by lipofuscin but not by macular pigment, and determining a melanin absorption coefficient based on the baseline AFI image;

converting the melanin absorption coefficient from the second wavelength to the first wavelength to provide converted melanin value; and subtracting the converted melanin value from the primary MPOD measurement to find a corrected MPOD.

5. The method of claim 4, wherein the first wavelength is 488 nm±5% and the second wavelength is 600 nm±5%.

6. The method of claim 4, wherein converting the of melanin absorption coefficients includes applying compensation factors for absorption differences between the second wavelength and the first wavelength.

7. The method of claim 4, wherein the corrected MPOD is calculated using a mathematical formulation that accounts for absorption coefficients and includes a weighted difference between logarithms of respective intensity ratios at the first wavelength and the second wavelength.

8. The method of claim 1, wherein the corrected MPOD is calculated using a mathematical formulation that accounts for absorption coefficients and includes a weighted difference between logarithms of respective intensity ratios at the first wavelength, the second wavelength, and the third wavelength.

* * * * *